United States Patent [19]
Archer et al.

[11] Patent Number: 5,976,547
[45] Date of Patent: Nov. 2, 1999

[54] ANALGESIC AND ANTIPHLOGISTIC COMPOSITIONS AND THERAPEUTIC WRAP FOR TOPICAL DELIVERY

[75] Inventors: Heidi K. Archer, Sterling, Va.; Mitchell S. Pettit, Bethesda, Md.

[73] Assignee: Niblick Pharmaceuticals, Inc., Washington, D.C.

[21] Appl. No.: 08/837,761

[22] Filed: Apr. 22, 1997

[51] Int. Cl.⁶ ............................................. A61K 35/78
[52] U.S. Cl. ................... 424/195.1; 514/783; 514/947; 514/964
[58] Field of Search ................ 424/195.1; 514/783, 514/947, 964; 602/42, 48, 58, 60

[56] References Cited

U.S. PATENT DOCUMENTS

| | | | |
|---|---|---|---|
| 3,832,343 | 8/1974 | Majoie | 260/236.5 |
| 4,358,286 | 11/1982 | Grollier et al. | 8/405 |
| 4,455,146 | 6/1984 | Noda et al. | 604/897 |
| 4,460,488 | 7/1984 | Grollier et al. | 252/89.1 |
| 4,474,753 | 10/1984 | Haslam et al. | 424/78 |
| 4,557,934 | 12/1985 | Cooper | 424/128 |
| 4,569,839 | 2/1986 | Grollier et al. | 424/74 |
| 4,684,522 | 8/1987 | Marissal et al. | 424/195.1 |
| 4,849,214 | 7/1989 | Ruiseco | 424/74 |
| 4,927,408 | 5/1990 | Haak et al. | 604/20 |
| 4,938,960 | 7/1990 | Ismail | 424/195.1 |
| 4,973,473 | 11/1990 | Schneider et al. | 424/63 |
| 5,006,338 | 4/1991 | Luenemann | 424/195.1 |
| 5,043,153 | 8/1991 | Vidéki et al. | 424/49 |
| 5,057,500 | 10/1991 | Thornfeldt | 514/53 |
| 5,080,646 | 1/1992 | Theeuwes et al. | 604/20 |
| 5,085,870 | 2/1992 | Seguin et al. | 424/547 |
| 5,120,544 | 6/1992 | Henley | 424/443 |
| 5,162,037 | 11/1992 | Whitson-Fischman | 600/12 |
| 5,167,616 | 12/1992 | Haak et al. | 604/20 |
| 5,176,913 | 1/1993 | Honerlagen et al. | 424/195.1 |
| 5,260,066 | 11/1993 | Wood et al. | 424/447 |
| 5,271,942 | 12/1993 | Heverhagen | 424/451 |
| 5,322,689 | 6/1994 | Hughes et al. | 424/401 |
| 5,474,783 | 12/1995 | Miranda et al. | 424/448 |
| 5,478,567 | 12/1995 | Nakagawa et al. | 424/535 |
| 5,478,579 | 12/1995 | Sawruk | 424/535 |
| 5,482,965 | 1/1996 | Rajadhyaksha | 514/452 |

FOREIGN PATENT DOCUMENTS

| | | |
|---|---|---|
| 9404286 | 12/1996 | Brazil . |
| 2504009 | 10/1982 | France . |
| 3316597 | 4/1984 | Germany . |
| 60126 | 8/1992 | Hungary . |
| 08099858 | 4/1996 | Japan . |
| 93194 | 12/1987 | Romania . |
| 99921 | 9/1990 | Romania . |
| 110906 | 5/1996 | Romania . |

OTHER PUBLICATIONS

Tiger Medicated Plaster, manufactured for Tiger Medicals, Ltd., Singapore by Teikoku Seiyaku Co., Ltd., Japan, May 16, 1997.

Tiger Medicated Plaster –RD, manufactured for Tiger Medicals, Ltd., Singapore by Teikoku Seiyaku Co., Ltd., Japan, Jun. 10, 1997.

Lyss et al., "Helenalin, an anti–inflammatory sesquiterpene lactone from Arnica, selectively inhibits transcription factor", Biol. Chem., vol. 378(9): 951–961, 1997.

Hall et al., "Anti–inflammatory agents; IV. Structure activity relationships of sesquiterpene lactone esters derived from helenalin", Planta Med., vol. 53(2): 153–156, 1987.

Hall et al., "Antiinflammatory activity of sesquiterpene lactones and related compounds", J. Pharm. Sci., vol. 68(5): 537–542, 1979.

Ice Ch'i Massage Cream, *Product Alert*, Jul. 31, 1995.

Bastos et al., *Cienc. Cult (Sao Paolo)*, vol. 39(5–6): 551–553, 1987.

Gora et al. *Herba Hung.*, vol. 19(1): 165–171, Abstract Only, 1980.

Homeolab USA Inc., *Product Alert*, Abstract Only, Jul. 14, 1997.

Now Foods, *Product Alert*, Abstract Only, Aug. 25, 1997.

Zim's Crack Creme, *Product Alert*, Abstract Only, Apr. 28, 1997.

The Merck Index, Twelfth Ed. (pp. 281,282,661,679,680, 776,777,903,905,936,937,996,1168), 1996.

Ansel et al. *Pharmaceutical Dosage Forms and Drug Delivery Systems*, pp. 357–359, 1995.

Tyler, Varro. The Honest Herbal: A Sensible Guide to the Use of Herbs and Related Remedies, Third Ed., pp. 35–37, 1993.

*Primary Examiner*—Howard C. Lee
*Attorney, Agent, or Firm*—Spencer Fane Britt & Browne LLP

[57] ABSTRACT

The present invention relates to topical over-the-counter and prescription strength analgesic and antiphlogistic blended compositions which are useful for reducing inflammation and providing relief from both peripheral and central pain as well as to a flexible therapeutic wrap for topical delivery of said blended compositions. More particularly, the invention is a blended composition comprising from about 3% to about 30% by weight of extract of arnica montana in combination with an effective amount of one or more therapeutic or pharmaceutical agents selected from the group consisting of menthol crystal, camphor, oil of mint, eucalyptus oil, guaifenesin, non-steroidal anti-inflammatory medications, topical analgesics, or transdermal opioid analgesics blended in either a pluronic lecithin organogel (PLO) or a petrolatum base. The particular agents selected and the percent composition of each selected ingredient in a given blend being determined by the needs and sensitivities of the given patient.

35 Claims, No Drawings

ANALGESIC AND ANTIPHLOGISTIC COMPOSITIONS AND THERAPEUTIC WRAP FOR TOPICAL DELIVERY

BACKGROUND OF THE INVENTION

1. Field of the Invention

The present invention relates to topical over-the-counter and prescription strength analgesic and antiphlogistic blended compositions which are useful for reducing inflammation and providing relief from both peripheral and central pain as well as to a flexible therapeutic wrap for topical delivery of said blended compositions. More particularly, the invention is a blended composition comprising from about 3% to about 30% by weight of extract of arnica montana in combination with an effective amount of one or more therapeutic or pharmaceutical agents selected from the group consisting of menthol crystal, camphor, oil of mint, eucalyptus oil, guaifenesin, non-steroidal anti-inflammatory medications, topical analgesics, or transdermal opioid analgesics blended in either a pluronic lecithin organogel (PLO) or a petrolatum base. The particular agents selected and the percent composition of each selected ingredient in a given blend being determined by the needs and sensitivities of the given patient.

2. Background of the Invention

A wealth of problems are known to be associated with the oral ingestion of pharmaceutical agents. For instance, due to sensitivities, many patients experience gastrointestinal irritation and intolerance from a single dose. Many others develop such intolerance as a result of prolonged treatment or develop other more severe gastrointestinal irritations such as ulceration. Further, patients present with widely differing metabolisms resulting in unpredictably variable rates of absorption. In addition, any oral treatment carries with it often unpredictable risks for side effects.

The risks and problems associated with oral introduction of medication are magnified when treating chronic pain such as peripheral neuropathic pain associated with diseases such as diabetes melitis, chronic renal failure, myeloma, cancer, and hypothyroidism. Repeated doses of oral medication are known to compound any negative effect on the stomach and intestinal tract. Moreover, many of the patients suffering from chronic illnesses are senior citizens who are even more susceptible to the risks and side effects from oral medication. Similarly, when a child presents with acute or chronic illness, it is particularly desirable to avoid the risks of side effects and the damage caused from repeated ingestion of medication.

Additionally, many pain medications and muscle relaxants given orally have undesirable effects on cognition and level of consciousness. A patient who suffers pain but must work, drive, and/or care for children places himself and others at risk while taking theses medications. These topical preparations allow for pain relief without undue risk of undesired sedation and altered cognition.

Another disadvantage of oral medication is its frequent ineffectiveness in treating specific types of pain such as the phantom limb pain associated with amputations. One explanation for this ineffectiveness is that oral medication provides no stimulation of the nerve endings to disrupt or stimulate the interrupted signal from the limb to the brain.

Delivery of pharmaceutically active agents through the skin avoids many of these risks and disadvantages. For instance, transdermal medication is parenteral, thus avoiding problems related to gastrointestinal irritation. Further, with topical administration, variances in absorption and metabolism rates cease to be a consequential factor and the risk of potential side effects is greatly reduced. In addition to avoiding many of the disadvantages associated with oral ingestion of medication, topical delivery has some distinct and important advantages. First, by medicating through the skin, a more even and continuous dosage of medication may be administered over a longer period of time. Further, such treatment provides more immediate, as well as more physically and psychologically rewarding, relief, as it may be applied directly to site of the pain, whether that pain be local in nature or a generalized pain with local manifestations. As discussed, localized application and sensitization is particularly important in cases involving amputation. Yet, although direct application may be to a local site, the medication is introduced and acts systemically.

In spite of the obvious advantages in providing medications topically, it has been difficult to find compositions and delivery methods which are effective for this purpose due to the nature of skin as a defensive barrier for the body. After all, one of the main functions of skin as an organ of the body is to obstruct toxic materials and pathogens from entering the body while retaining desired physiological fluids and nutrients within the body. For this reason, the skin is highly impermeable, creating a challenge to the percutaneous introduction of pharmaceutically active agents. Thus, a search continues to discover methods of delivery or compositions which will be successful in transporting an effective dosage of medication across this natural barrier.

The problems with topical delivery are really two-fold. First, as just described, there is the challenge of finding a composition and method of application which permits transport across the skin's natural barrier. The second problem is focused on the mechanics of delivering medication to a flexible, mobile, and sensitive surface such as the skin. To encourage a patient's cooperation with systematic and often long-term treatment, pharmaceutical or therapeutic agents must be delivered in a way that will be comfortable and even rewarding to the patient. Further, it is important that the method of delivery ensure that the active agents are kept securely in place against the skin long enough to permit the desired penetration without unduly affecting the patient's mobility. Finally, safety is a concern, particularly when treating pediatric or geriatric patients in whom there is risk of ingestion of the medication or plasticized portions of the wrap.

There have been a variety of approaches suggested for addressing the first of these challenges—enhanced penetration. For instance, it has long been known that the introduction of an electrical charge at the point of transdermal transport may assist the penetration of certain medications. Recent improvement patents in this area are U.S. Pat. No. 4,927,408 to Haak and U.S. Pat. No. 5,080,646 to Theeuwes et al. The basic principle here is to effect the system electrochemically so as to enhance penetration. The disadvantages of such a system, however, are in the need for additional specialized equipment and/or chemicals beyond that which is needed to medicate. These additional requirements bring with them risks and costs.

Another approach for achieving increased penetration of pharmaceutically active agents is through the use of chemical enhancers. An effective amount of these enhancing chemicals are mixed with the desired medicinal agent before it is applied to the skin resulting in more effective penetration. It is taught that these chemical enhancers are effective in speeding and increasing the penetration of the medication due to their chemical similarity to the highly impermeable outer layer of the skin. U.S. Pat. No. 5,482,965 to Rajadhyaksha teaches the use of amino alcohol derivatives to achieve enhanced membrane penetration. Similarly, U.S. Pat. No. 4,557,934 discloses another series of chemicals which are effective for this purpose. Once again, however, as in the use of electrical charge, the use of chemical enhancers has the disadvantage of requiring something in addition to the ingredients needed for treatment. Addition of any medically unnecessary chemical ingredient carries with it an increased risk for reaction.

It would be beneficial, therefore, to discover a therapeutically active ingredient or a combination of ingredients which would accomplish penetration without outside influence. This is particularly needed in the treatment of neuropathic pain of the type associated with conditions such as arthritis or diabetes. Anti-inflammatories and pain killers such as ketoprofen or lidocaine applied topically to an area affected by pain may provide some local relief but there is very little deep penetration of such non-steroidal anti-inflammatory and/or analgesic medications and, therefore, little, if any, relief from more generalized neuropathic pain. The inventors herein have unexpectedly discovered that the extract of an herb called arnica montana, in combination with certain other therapeutic agents such as analgesics, warms and increases capillary blood flow to the treatment area, thereby improving absorption of the active ingredients. This synergistic effect results in enhanced penetration of the skin to provide pain relief both for local and diffuse pain conditions such as diabetes or myeloma. Arnica montana (commonly known as mountain tobacco) is an herb which grows on the mountains of Switzerland and is also cultivated elsewhere in the world. The medicinal value of various extracts of the herb has been recognized for centuries in the treatment of numerous illnesses, however, there is no consensus as to the active principle behind its reported effectiveness. Nevertheless, arnica montana has been cited as useful in a wide variety of applications. For example, a relatively recent patent to Sawruk, U.S. Pat. No. 5,478,579, teaches a method for inducing and enhancing the absorption of calcium into bone by combining the calcium with an effective dose of flavonol aglycone glycoside. Sawruk identifies arnica montana as a significant source of this chemical component. In this instance, it is opined that the flavonol aglycone glycosides assist in absorption of calcium through a chelation delivery system. Other oral applications of arnica extracts are rare, however, because it has been reported that arnica has a harmful effect on the heart and may also effect the nervous system negatively at high doses.

Topical uses for extracts of arnica montana are, by far, the most common and attribute a wide range of attributes to the herbal extract. For example, the addition of extract of arnica is recommended in U.S. Pat. No. 5,271,942 to Heverhagen which discloses an agent for reducing hair growth on the human body. It is suggested that arnica extract has "astringent, tonic, soothing and wound-healing effects" and should, therefore, be added to the hair reduction agent to compensate for cases of sensitive skin. These same soothing and healing qualities are recognized in U.S. Pat. No. 4,569,839 to Grollier et al. for use in a cosmetic treatment for the hair and skin. Perhaps the most common topical use for arnica is in the treatment of hematomas as taught in U.S. Pat. No. 3,832,343 to Majoie et al. Arnica's effectiveness in this instance is attributed to its effectiveness in preventing coagulation of blood. In Ismail, U.S. Pat. No. 4,938,960, extract of arnica montana is recognized as having the ability to promote blood circulation and is, therefore, a suggestive additive to an agent for treatment and protection of the skin on the theory that the arnica will increase the action of the vitamin E in the composition. Addition of extract of arnica is also taught for a variety of cases where the desired result is a reduction of inflammation and/or edema such as U.S. Pat. No. 5,043,153 to Videki et al. for compositions for the treatment of parodonthopathy and U.S. Pat. No. 4,795,638 to Ayache et al. and U.S. Pat. No. 4,684,522 to Marissal et al., both directed to compositions to reduce adipose swelling and cellulite, inferring an anti-inflammatory characteristic to the herb.

None of these references recognize arnica as useful in enhancing penetration of the skin or as an effective agent in providing neuropathic pain relief. U.S. Pat. No. 5,162,037 to Whitson-Fischman teaches the use of extract of arnica montana as one of many components in an herb-based homeopathic medicament for the treatment of chronic muscular and joint pain. Whitson-Fischman, however, does not specify the role of arnica in the component mix disclosed herein. Further, the method taught in Whitson-Fischman involves delivery of the homeopathic medicant mix in three separate phases: an injectable dose delivered to specified acupuncture points; a topical dose delivered by means of a transdermal patch applied directly over appropriate acupuncture points; and orally. In addition, in each of these delivery methods, the medications delivered to the body are magnetically stimulated at the time of introduction to assist in absorption and effectiveness. The invention herein rests in part on the discovery that extract of arnica montana, in combination with other selected components, warms and increases capillary blood flow, thereby improving absorption of other active ingredients simply through topical delivery according to the proposed delivery method and without the need for other stimulus.

Once penetration and effective pain relief is achieved, the next significant concern in achieving effective topical application is keeping the therapeutic agent comfortably and productively in place for the length of time required to achieve the desired penetration and results. The difficulties here focus on the flexibility of the skin, the mobility of the patient, the sensitivity of the skin, and other related considerations such as sterility and the need to protect clothing and bedding from the medication. For these reasons, it is desirable that topical therapeutic compositions be of a consistency that will easily accommodate the skin's flexibility, yet stay in place as the patient moves about. The consistency of the medicant, therefore, should be pliable but tacky. Further, it is important that the treating composition stay in place for the duration of treatment yet be able to be comfortably removed and cleaned away between treatments. Such a support, whether it be a bandage, patch, or wrap, should be easily removable, offer protection to clothing and bedding, and support the active ingredients in such a way that they achieve the best possible contact with and penetration into the skin. Moreover, it is important that the pharmaceutical composition be sterile and that any bandage or cover placed over the medication is also sterile as well as providing a good support for the therapeutic agents. Finally, safety issues must be addressed. Thus, the medication must be offered in a composition without plastic covering and with low enough dosage to be non-toxic for a pediatric and geriatric population where there is a risk of ingestion of the medicant or any removable plasticized material.

From the foregoing, it will be appreciated that what is needed in the art are topical compositions which will effectively penetrate the skin's barrier, delivering effective relief from both localized and generalized pain, without the need for expensive andlor risky supplemental enhancers such as non-active chemical additives, or electrical, magnetic, or heat stimulation. Further, a method of topical delivery is needed that will effectively deliver the medication over the period needed for penetration without affecting the comfort, safety, or mobility of the patient.

Accordingly, it is a primary object of the present invention to provide safe and effective localized and generalized pain relief through topical delivery of therapeutic agents.

It is a further object of the present invention to provide a means of delivering effective dosages of therapeutic agents transdermally.

A still further object is to provide pain relief topically, and thereby without the risks of sedation and cognitive effects associated with orally administered pain relievers and muscle relaxants.

Another object is to provide pain relief to geriatric, pediatric, and cancer patient populations unable to tolerate orally administered medications.

Yet another object is to provide pain relief to patients who have not achieved adequate pain control/management via oral medications (e.g. amputee).

Still another object is to provide means for delivering effective dosages of therapeutic agents to sites of localized pain and inflammation.

Another object of this invention is to maintain relatively constant dosages of therapeutic agents to sites of pain.

Yet another object of this invention is to provide a protective, comforting cover to sites of local manifestation of pain and/or inflammation.

Another object of this invention is to provide a flexible, protective wrap which will deliver effective dosages of medication without inhibiting patient mobility.

A final object is to provide a controlled-released therapeutic wrap constructed of inexpensive materials.

SUMMARY OF INVENTION

This invention relates to new topical therapeutic compositions for treatment of inflammation and/or pain, both localized and diffuse, and to a flexible, protective wrap for effective topical delivery of said compositions. The antiphlogistic and analgesic compositions within the scope of this invention are comprised of an extract of arnica montana in combination with one or more therapeutic or pharmaceutical agents selected from the group consisting of menthol crystal, camphor, oil of mint, eucalyptus oil, guaifenesin, non-steroidal anti-inflammatory medications, topical analgesics, or transdermal opioid analgesics blended in either a pluronic lecithin organogel (PLO) or a petrolatum base. Menthol crystal, camphor, mint oils, lidocaine, and eucalyptus oil are known to provide analgesia and a local warming effect due to increased blood flow. As indicated previously, it has also been suggested that arnica may enhance blood flow. The inventors herein have discovered a synergistic effect by combining arnica extract with these selected ingredients to greatly increase absorption of the effective ingredients resulting in a much more effective reduction of pain and inflammation. Not only is there localized pain relief at the site of topical application, but this combination delivers unexpected systemic pain relief. Guaifenesin, an ingredient in cough syrup, when applied topically, offers relief in many patients by decreasing muscle spasm. Its absorption and effectiveness are also assisted by the effect of the blend. Where more substantial pain or swelling exists, non-steroidal anti-inflammatories or transdermal opioids may be indicated. Again, absorption and, thus, effectiveness of these ingredients is assisted by the overall combination of the blend. The particular agents selected and the percent composition of each selected ingredient in a given blend are determined by the needs and sensitivities of the given patient.

These blended compositions have been found effectively to penetrate the skin and provide both local and systemic relief for local, chronic and/or diffuse pain, including the neuropathic pain encountered with diseases such as diabetes and myeloma, or following limb amputation. These results are achieved when these blended compositions are placed against the skin, either at a site of localized pain or at a local manifestation of neuropathic or other diffuse pain, and maintained in close contact with the skin for an effective period of time. The pluronic lecithin organogel (PLO) or petrolatum base vehicle of the therapeutic blends assists in maintaining the therapeutic blend in the required contact with the skin contact as it provides a consistency which is flexible, remains in close contact with the skin, and will not run off of the desired application area. The pluronic lecithin organogel (PLO) allows water soluble ingredients to be put in solution in the pluronic component, the oil-soluble ingredients are blended in the lecithin, then the two are mixed and come out as the organogel which can be applied to the backing of a therapeutic wrap for delivery to the patient as disclosed herein.

Specifically, further to assist in effective application and duration of treatment with said therapeutic blends, a therapeutic wrap is used as a vehicle for topical application. This wrap ensures that the blend is kept in close contact with the skin for the full duration required to provide the desired pain relief while causing little restriction to the patients mobility. The therapeutic wrap consists of a support structure which acts as a platform for supporting the blend against the skin. The chosen therapeutic blend is spread on and/or impregnated in one side of the support material. Said support material should be of a consistency such that it will readily accept and hold the therapeutic blend in place next to the skin and freely release its therapeutic and/or pharmaceutical agents to the skin. Further, said support should bend and flex with the patient, molding to the skin in such a way as to keep the therapeutic/pharmaceutical agents in close proximity with the skin while permitting the patient a wide range of mobility during treatment. Finally, the therapeutic wrap should be easily removable without discomfort to the patient.

Where an open weave material is used as a support, a backing material may be placed on the side of the support material opposite the deposited therapeutic blend. Such backing material will add to the comfort of the wrap and assist in preventing "bleed through" of the therapeutic blend, thus serving as a protective shield for clothing, bedding, and the like. This backing could be a thin layer of cotton or a plastic film covering, plastic not being recommended for pediatric or geriatric wraps due to the danger of ingestion. The backing serves the additional purpose of reducing local heat dissipation, thereby adding to the warming effect of the wrap.

DESCRIPTION OF THE PRESENTLY PREFERRED EMBODIMENT

The present invention is the result of research with extract of the herb arnica montana in combination with various other pharmaceutical and/or therapeutic agents for use in the topical treatment of both peripheral and central pain, including but not limited to, acute and post-operative pain, pain of osteoarthritis, rheumatoid arthritis, orthopedic pain after trauma, skeletal muscle pain, low back pain, myofascial pain, phantom pain and other phenomena following amputation, peripheral neuropathies, sympathetically maintained pain, cancer pain (including pain following radiation and chemotherapy), and pediatric and geriatric pain of various etiologies. While there are numerous topical analgesics which have been shown effective in the treatment of localized pain, effective topical treatments for diffuse pain such as neuropathic pain are lacking. The challenge was to determine a therapeutic blend that would: 1) effectively penetrate the skin barrier, 2) provide measurable pain relief not just for localized pain but also for diffuse pain such as the neuropathic pain associated with diseases such as diabetes and myeloma, 3) have a consistency that was tacky enough to keep the medicament moist and on the desired treatment area long enough to allow for penetration, 4) bend and flex with the skin, and 5) have minimal side effects.

In one aspect, the invention is premised on the discovery that topical administration of a blend comprising from about 3% to about 30% of arnica montana extract and an effective amount of one or more therapeutic or pharmaceutical agents selected from the group consisting of menthol crystal, camphor, oil of mint, eucalyptus oil, or lidocaine effectively meets these criteria in a non-prescription formulation.

The arnica montana extract used in the compositions according to the present invention is commercially available and can be provided in the form of a tincture (U.S. pharmacopeia) or glycol extract, or dry residue. Its concentration in these blends, expressed on a dry basis, can range from about 3% to about 30% relative to the total weight of the composition. Preferably, in accordance with the present invention, arnica montana extract is employed at a concentration of about 5% to about 10% by weight.

The selected additional ingredients and the concentrations thereof should be therapeutically effective and are determined by the needs and sensitivities of the intended patient. In most cases, best results are achieved within a range from about 3% to about 10% by weight of menthol crystal and camphor, from about 3% to about 20% by weight of mint oil, from about 2% to about 5% by weight of eucalyptus oil, and from about 5% to about 10% by weight of lidocaine. One or more of these ingredients may be blended with the arnica extract to provide the desired result. Addition of from about 5% to about 20% by weight of guaifenesin may be indicated where muscle spasm is a problem.

Where oil of mint is a selected ingredient, the preferred choices are peppermint or wintergreen oil. On the other hand, some patients find the strong scent of some of these ingredients offensive, especially in the workplace. Thus, according to one aspect of the invention, a non-scented therapeutic blend is created by omitting the menthol crystal, camphor, oil of mint, and eucalyptus oils.

Once the selected combination of ingredients are chosen, they are blended in a pluronic lecithin organogel (PLO) or a petrolatum base to create a tacky consistency that will cause the therapeutic blend to "stick" to the skin and/or the therapeutic wrap described herein.

In still another aspect of the invention, a prescription strength therapeutic blend may be created for treatment of more severe pain or inflammation. The prescription strength blend comprises from about 3% to about 30% by weight of extract of arnica montana in combination with an effective amount of one or more therapeutic or pharmaceutical agents selected from the group consisting of menthol crystal, eucalyptus oil, topical analgesics, non-steroidal anti-inflammatory medications, or transdermal opioid analgesics. Again, as in the over-the-counter blend, guaifenesin may also be added to relive muscle spasm.

Preferably, any non-steroidal anti-inflammatory medication included will be in the concentration of from about 5% to about 20% by weight. As with lidocaine in the over-the-counter blend, the suggested concentrations for the topical analgesics of the prescription strength blend are from about 5% to about 10% by weight. While there are many effective choices from the groups of non-steroidal anti-inflammatory medications and topical analgesics, particularly effective choices are ketoprofen as a non-steroidal anti-inflammatory and lidocaine as the topical analgesic.

Preferred concentrations of the other potential ingredients range from about 3% to about 10% by weight of menthol crystal, from about 2% to about 5% by weight of eucalyptus oil, and from about 5% to about 30% of guaifenesin. Where transdermal opioid analgesics are used, it is preferable that the dosage be from about 15 mcg/cc to about 50 mcg/cc. Opioids are strong analgesics which are believed to increase the patient's pain tolerance and limit perception of suffering, yet permit the patient to recognize the presence of pain so they will not engage in harmful activity. Again, although there are many transdermal opioid analgesics which would be appropriate, fentanyl or ketamine are the preferred choices for these topical applications due to availability, reasonable cost, and efficacy.

As with the over-the-counter wrap, the specific choice of ingredients and concentrations are dictated by the sensitivities and needs of the given patient as well as the source or type of pain. The case studies presented at the end of this description section offer some further insight into specific blends that have been effective in given situations, although these case studies and the formulations described therein are offered merely as illustrative and not offered by way of limitation.

As in the non-prescription blend, the selected ingredients are blended in a base vehicle such as pluronic lecithin organogel (PLO) or petrolatum. The PLO or petrolatum provides a tacky characteristic to the blend such that it takes on its own adhesive strength and will adhere and stay in place on the skin.

This tacky quality also makes the blend difficult to work with and apply, however, because it will stick to the fingers, clothing, and bedding as well. Thus, it is important to find a method for delivery which will assist in application and ensure that the active ingredients are kept in close contact with the treatment site long enough to achieve the desired penetration and results.

The wrap of this invention is prepared by spreading and/or impregnating a selected therapeutic blend onto one side of a support material and then placing the medicated side of the support against the skin at the selected treatment site. The support material should be flexible to accommodate the bend and flex of the skin and the mobility of the patients. The size and shape of the chosen support is determined by the treatment site. The material chosen for the support is selected from the group of supports consisting of woven fabrics (man-made or natural), non-woven fabrics (man-made or natural), polymer foams, naturally occurring or synthetic sponges, polyester films, poly-vinylidene chloride films, polypropylene films, polyurethane films, or polyamide films. Open weave cotton gauze is a preferable support material because it is soft against the skin, flexible, and its open weave structure easily accepts, holds, and releases the therapeutic blend to the skin.

In another aspect of the invention—a backing material—is included on the side of the support opposite the therapeutic blend. This backing material serves as a protective shield for clothing, bedding, and the like by preventing bleed through of the therapeutic blend. A suitable backing material is one that is soft and flexible. In practice, cotton felt or batting has proven to be a preferable choice as it is comfortable, relatively safe, non-irritating and provides a good protection for clothing and bedding. Plasticized backing material may be desirable in some situations due to its added protective features, however, plasticized materials are not recommended for either the geriatric or pediatric population where oral ingestion of the material is a risk.

Therapeutic wraps consisting of preselected blends may be prepared in advance of use by covering the support-carried therapeutic blend with a releasable sheet. A plasticized material works well for this purpose but the releasable sheet may be any material which will not take a substantial amount of the therapeutic blend with it when it is peeled away from the medicated support. Here again, safety is a concern and a plasticized support sheet is not recommended where it may be accidentally ingested by a geriatric patient suffering from dementia or the like or a pediatric patient.

Once the medication is in place, the therapeutic wrap is sealed in a protective pouch where it may be stored until its use. If long-term storage is intended, the pouch should be as airtight as possible as exposure to air may affect the effectiveness of some of the active agents in the blends. A sealable foil lined pouch or plasticized bag work well for this purpose. To use the wrap, the pouch is opened, the wrap is removed, the releasable sheet is pulled away, and the medicated side of the support is positioned against the treatment site on the skin.

The therapeutic wraps so described are excellent in tackiness, adhesiveness, ease of removal, flexibility and other physical stability, as well as in dischargeability of the medicine and pharmacological effects, and they cause very few side reactions such as formation of a rash.

The following clinical cases demonstrate the effectiveness of the therapeutic blends and wrap of the invention:

Case I—Pediatric Sports Injury.

A five-year-old child who sustained an injury to his right ankle during a soccer match. His parents iced the ankle, as appropriate, for the initial 24 hours following the injury, but brought him for evaluation due to persistent pain and swelling. He presents with painful range of motion of the right ankle, significant soft tissue edema, small hematoma, and tenderness to palpation along the length of the right talofibular ligament. No sensory deficit is present and pedal pulses are symmetrical bilaterally. Diagnosis is sprain of right talofibular ligament with acute hematoma.

The treatment plan for the patient is to continue icing the area for 20 minutes three times per day, to rest the ankle by avoiding weight bearing, to elevate the ankle to help decrease edema, and to provide compression with an elastic bandage, again to control swelling. The parents are instructed NOT to treat their son with aspirin or anti-inflammatory medications due to their potential to increase bleeding and thereby extend the hematoma. Instead, the child is treated with a therapeutic wrap according to the present invention containing:

10% arnica montana
10% ketoprofen
10% menthol crystal
5% camphor
5% oil of mint
10% lidocaine
mixed into a pluronic lecithin organogel or a petrolatum base.

The above wrap provides pain relief, edema reduction, increased blood perfusion to the area to decrease inflammation. The wrap is applied directly to the affected site and the elastic compression bandage is applied over the therapeutic wrap. The wrap and bandage are changed twice per day, at which time gentle range of motion within pain tolerance is performed.

After five days of treatment, the acute pain and inflammation are significantly reduced. Minimal residual edema is present and the hematoma is resolving nicely. The patient is able to partially weight bear without pain. He is enrolled in physical therapy to commence appropriate rehabilitation program, with patches applied on an as-needed basis for soreness or recurrent edema following therapeutic exercise and gait training.

Case II—Diabetic Peripheral Neuropathy.

A 55-year-old female with a 24-year history of insulin dependent diabetes melitis presents with severe peripheral neuropathy. She has an associated sleep disorder, complaining of lower extremity paresthesias, numbness, and hyperesthesia most severe during the night. The patient reports that her daughter is a nurse who works the night shift, and the patient is home caring for her daughter's six-month-old infant while her daughter is at work each night. Previous physicians have recommended multiple medications including anti-depressants, anti-convulsants, and muscle relaxants but the patient has been unwilling to take these medications due to their side effect, without exception, of central nervous system sedation. She is extremely concerned with failing to awaken, or having altered cognition, should her grandchild need her during the night.

The patient is treated with therapeutic wraps applied locally to the distal lower extremities before bed each night. The wrap contains:

10% arnica montana
10% menthol crystal
10% fentanyl
10% guaifenesin
mixed into a pluronic lecithin organogel or petrolatum base.

The patient's painful symptoms are relieved and she is able to sleep through the night, confident that she will be able to awaken promptly and alertly in the event of an emergency with her grandchild.

Case III—Lower Back Pain.

A 36-year-old computer programmer sustains a lumbosacral back strain injury while twisting and lifting an awkward and heavy box containing a computer printer onto a desk. MRI reveals a small herniated disc without lateralization and physical exam lacks focal neurological deficit. Tenderness and spasm of the paraspinal muscles is, however, severe. Surgical intervention is not appropriate, but the pain is severe and the patient does not want to lose time from work. Prolonged sitting aggravates his pain and spasm, and he reports the muscle relaxants given to him in the emergency room made him "too groggy" to work.

The patient is treated with appropriate physical therapy, is educated in back protection, and an ergonomic assessment of his work site is performed. His pain is managed with a wrap containing the following:

10% arnica montana
10% ketoprofen
10% lidocaine

10% oil of mint

20% guaifenesin (high percentage to control acute spasm effectively)

Mixed in pluronic lecithin organogel or a petrolatum base. (Please note that the menthol crystal and camphor are not included due to the patient's preference for an unscented wrap for use in the workplace.)

Case IV—Breast Cancer Survivor with Post-Surgical

Pain—A 42-year-old female presents status post right modified radical mastectomy and a complete cycle of chemotherapy and radiation therapy. She complains of severe pain related to persistent right upper extremity lymphedema, a common problem following lymph node resection. The patient is extremely intolerant of systemic medications and has trouble complying with the multiple medications and their side effects of nausea and vomiting, preferring to avoid adding yet another medication to her regimen.

The patient is treated with appropriate physical and occupational therapy and a wrap consisting of:

10% arnica montana

10% lidocaine

10% menthol crystal

5% oil of mint

10% guaifenesin mixed into a pluronic lecithin organogel or a petrolatum base.

The patient returns for follow-up in two weeks, reporting only partial improvement of her symptoms of right upper extremity edema and discomfort. She is still not sleeping well. The patient is prescribed a more powerful wrap containing the above ingredients but replacing the lidocaine with 10% ketamine. The patient returns for follow up one week later and is very pleased with her improved pain management and her ability to sleep through the night. She is especially happy to have pain relief without systemic side effects.

Case V—Osteoarthritis Patient.

A 75-year-old patient with history of duodenal ulcer during previous treatment with non-steroidal anti-inflammatories is having progressive limitation of functional mobility due to severe left knee pain. While a knee replacement was considered by the orthopedic surgeon, the patient was deemed not to be a surgical candidate due to his age and multiple medical problems including compromised cardiac status. The patient cannot safely be treated with anti-inflammatories due to risk of recurrent GI bleed.

The patient is treated with a therapeutic blend containing:

10% arnica montana

10% lidocaine

10% menthol crystal

5% oil of mint

5% fentanyl

The patient returns for follow-up and reports excellent pain relief. Now that adequate pain management has been achieved without undue risk of side effects, the patient is motivated to pursue a physical therapy program. The patient is able to tolerate a progressive strengthening program focusing on the quadriceps muscles, "the guardians of the knee." With the newly-strengthened quadriceps, the joint pain in the knee is decreased, and the patient's wrap is modified by eliminating the fentanyl. The continuation of his home exercise program and over the counter strength therapeutic wrap manages his pain and he maintains his desired level of functional mobility and independence.

Case VI—Amputee.

A 55-year-old patient with diabetes presents with severe phantom pain status post left below-knee amputation for a non-healing gangrenous ulcer. The etiology of the pain is likely in part due to sudden absence of motor and sensory nerve input to the brain from the severed peripheral nerves. Many medications have been tried but none has provided significant relief of this patient's symptoms. The phantom pain and phantom sensation also limit the patient's tolerance of his prosthesis, with subsequent lack of progress in gait training.

The patient is treated with a therapeutic wrap containing the following:

10% ketamine

10% arnica montana

5% camphor

10% menthol crystal

5% oil of mint mixed in a pluronic lecithin organogel or petrolatum base. The patient's phantom pain improves, and with the increased tolerance of a weight bearing and desensitization techniques to his residual limb, the cycle of aberrant pain perception is broken. The patient is tapered to an over-the-counter strength wrap as the ketamine is no longer indicated and, after several weeks, requires no further pain treatment.

It should be appreciated that the therapeutic blends and associated wraps of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. A therapeutic blend for topical treatment of pain consisting essentially of from about 3% to about 30% by weight of extract of Arnica montana in combination with an amount effective to ease systemic pain of at least one of the following:

(a) menthol crystal;

(b) camphor;

(c) oil of mint;

(d) eucalyptus oil;

(e) guaifenesin;

(f) lidocaine;

said combination being mixed into either a pluronic lecithin organogel (PLO) or a petrolatum base.

2. The therapeutic blend of claim 1 comprising from about 3% to about 10% by weight of menthol crystal.

3. The therapeutic blend of claim 1 comprising from about 3% to about 10% by weight of camphor.

4. The therapeutic blend of claim 1 comprising from about 3% to about 20% by weight of oil of mint.

5. The therapeutic blend of claim 1 comprising from about 2% to about 5% by weight of eucalyptus oil.

6. The therapeutic blend of claim 1 wherein said oil of mint is either wintergreen oil or peppermint oil.

7. The therapeutic blend of claim 1 comprising from about 5% to about 20% by weight of guaifenesin.

8. The therapeutic blend of claim 1 comprising from about 5% to about 10% by weight of lidocaine.

9. A therapeutic blend for topical treatment of pain consisting essentially of from about 3% to about 30% by weight of extract of Arnica montana in combination with an amount effective to ease systemic pain of at least one of the following:

(a) non-steroidal anti-inflammatory medications;
(b) topical analgesics;
(c) menthol crystal;
(d) guaifenesin;
(e) transdermal opioid analgesic;
(f) eucalyptus oil;
said combination being mixed in either a pluronic lecithin organogel (PLO) or a petrolatum base.

10. The therapeutic blend of claim 9 wherein said non-steroidal anti-inflammatory medication is ketoprofen.

11. The therapeutic blend of claim 9 comprising from about 5% to about 10% by weight of topical analgesics.

12. The therapeutic blend of claim 9 wherein said topical analgesic is lidocaine.

13. The therapeutic blend of claim 9 comprising from about 3% to about 10% of menthol crystal.

14. The therapeutic blend of claim 9 comprising from about 5% to about 30% of guaifenesin.

15. The therapeutic blend of claim 9 comprising from about 15 mcg/cc to about 50 mcg/cc of transdermal opioid analgesic.

16. The therapeutic blend of claim 9 wherein said transdermal opioid analgesic is fentanyl.

17. The therapeutic blend of claim 9 wherein said transdermal opioid analgesic is ketamine.

18. The therapeutic blend of claim 9 comprising from about 2% to about 5% by weight of eucalyptus oil.

19. A therapeutic wrap for delivering therapeutic blends for topical treatment of pain to the skin of mammals, said therapeutic blends consisting essentially of from about 3% to about 30% by weight of extract of Arnica montana in combination with an amount effective to ease systemic pain of at least one of the following:

(a) menthol crystal;
(b) camphor;
(c) oil of mint;
(d) eucalyptus oil;
(e) guaifenesin;
(f) lidocaine;
said combination being mixed into either a pluronic lecithin organogel (PLO) or a petrolatum base and delivered to said skin by said therapeutic wrap; said therapeutic wrap being prepared by spreading said therapeutic blends directly on one side of a support material and then covering the support-carried blend with a releasable material.

20. A therapeutic wrap according to claim 19 wherein the side of the support which is not spread with therapeutic blend is covered with a backing material to prevent the therapeutic blend from bleeding through the support.

21. The therapeutic wrap of claim 19 wherein said support material is cotton mesh gauze.

22. The therapeutic wrap of claim 20 where said backing material is cotton.

23. The therapeutic wrap of claim 19 wherein said releasable material is a plasticized sheet.

24. A therapeutic wrap according to claim 19 wherein said wrap is packaged in a sealed pouch.

25. The therapeutic wrap of claim 24 wherein said pouch is foil lined.

26. The therapeutic wrap of claim 24 wherein said pouch is a plastic bag.

27. A therapeutic wrap for delivering therapeutic blends for topical treatment of pain to the skin of mammals, said therapeutic blends consisting essentially of from about 3% to about 30% by weight of extract of Arnica montana in combination with an amount effective to ease systemic pain of at least one of the following:

(a) non-steroidal anti-inflammatory medications;
(b) topical analgesics;
(c) menthol crystal;
(d) guaifenesin;
(e) transdermal opiod analgesic;
(f) eucalyptus oil;
said combination being mixed into either a pluronic lecithin organogel (PLO) or a petrolatum base and delivered to said skin by said therapeutic wrap; said therapeutic wrap being prepared by spreading said therapeutic blends directly on one side of a support material and then covering the support-carried blend with a releasable material.

28. A therapeutic wrap according to claim 27 wherein the side of the support which is not spread with therapeutic blend is covered with a backing material to prevent the therapeutic blend from bleeding through the support.

29. The therapeutic wrap of claim 27 wherein said support material is cotton mesh gauze.

30. The therapeutic wrap of claim 28 where said backing material is cotton.

31. The therapeutic wrap of claim 27 wherein said releasable material is a plasticized sheet.

32. A therapeutic wrap according to claim 27 wherein said wrap is packaged in a sealed pouch.

33. The therapeutic wrap of claim 32 wherein said pouch is foil lined.

34. The therapeutic wrap of claim 24 wherein said pouch is a plastic bag.

35. The therapeutic blend of claim 9 comprising from about 5% to about 20% by weight of non-steroidal anti-inflammatory medications.

* * * * *

UNITED STATES PATENT AND TRADEMARK OFFICE
Certificate

Patent No. 5,976,547            Patented: November 2, 1999

On petition requesting issuance of a certificate for correction of inventorship pursuant to 35 U.S.C. 256, it has been found that the above identified patent, through error and without anydeceptive intent, improperly sets forth the inventorship.

Accordingly, it is hereby certified that the correct inventorship of this patent is: Heidi Archer, Sterling, Va.

Signed and Sealed this Fifth Day of December, 2000.

GARY GEIST
*Supervisory Patent Examiner*
Art Unit 1623

UNITED STATES PATENT AND TRADEMARK OFFICE
CERTIFICATE OF CORRECTION

PATENT NO. : 5,976,547
DATED : November 2, 1999
INVENTOR(S) : Heidi K. Archer

It is certified that error appears in the above-indentified patent and that said Letters Patent is hereby corrected as shown below:

On the Title page, item [54] delete --Mitchell S. Pettit Bethesda, MD --.

| | |
|---|---|
| In Column 3, Line 23, | Change "amica" to --arnica--; |
| In Column 3, Line 36, | Change "amica" to --arnica--; |
| In Column 4, Line 67, | Change "andlor" to --and/or--; |
| In Column 11, Lines 8 & 9, | Change "Breast Cancer Survivor with Post-Surgical Pain" to --Breast Cancer Survivor with Post-Surgical Pain--; |
| In Column 13, Line 3, | Change "Amica" to --arnica--. |

Signed and Sealed this

Sixth Day of March, 2001

*Attest:*

NICHOLAS P. GODICI

*Attesting Officer*     *Acting Director of the United States Patent and Trademark Office*